US011123260B1

(12) United States Patent
Arceneaux (10) Patent No.: US 11,123,260 B1
(45) Date of Patent: Sep. 21, 2021

(54) ANATOMICALLY ERECT PENILE PROSTHESIS WITH INTEGRAL SUSPENSORY MECHANISM

(71) Applicant: Gregory P Arceneaux, Waco, TX (US)

(72) Inventor: Gregory P Arceneaux, Waco, TX (US)

(*) Notice: Subject to any disclaimer, the term of this patent is extended or adjusted under 35 U.S.C. 154(b) by 0 days.

(21) Appl. No.: 16/872,719

(22) Filed: May 12, 2020

(51) Int. Cl.
*A61F 5/41* (2006.01)
*A61H 19/00* (2006.01)

(52) U.S. Cl.
CPC .............. *A61H 19/44* (2013.01); *A61F 5/41* (2013.01); *A61H 19/50* (2013.01); *A61F 2005/411* (2013.01); *A61H 2201/1645* (2013.01); *A61H 2201/1652* (2013.01)

(58) Field of Classification Search
CPC ...... A61F 5/41; A61F 5/451; A61F 2005/411; A61F 2005/414; A61F 2005/417; A61H 19/00; A61H 19/30; A61H 19/32; A61H 19/34; A61H 19/50; A61H 2201/1645; A61H 2201/1647; A61H 2201/165; A61H 2201/1652
See application file for complete search history.

(56) References Cited

U.S. PATENT DOCUMENTS

| 4,022,196 | A |   | 5/1977  | Clinton     |           |
|-----------|---|---|---------|-------------|-----------|
| 4,449,520 | A |   | 5/1984  | Palomar     |           |
| 4,471,772 | A | * | 9/1984  | Miller, Jr. | A61F 5/41 |
|           |   |   |         |             | 2/403     |
| 4,982,731 | A |   | 1/1991  | Lue         |           |
| 5,823,939 | A |   | 10/1998 | Tsagarakis  |           |
| 6,579,229 | B1|   | 6/2003  | Nan         |           |
| 6,749,558 | B1|   | 6/2004  | Brintle     |           |
| 7,611,456 | B2|   | 11/2009 | Jared       |           |
| 8,734,323 | B2|   | 5/2014  | Staffolani  |           |
| 8,764,629 | B2|   | 7/2014  | Braud       |           |
| 9,101,497 | B2|   | 8/2015  | Tan         |           |
| 9,649,190 | B2|   | 5/2017  | Mathies     |           |
| 9,649,249 | B1|   | 5/2017  | Green       |           |
| 10,314,761| B2|   | 6/2019  | Callow      |           |
| 10,398,558| B2|   | 9/2019  | Crabb       |           |
| 10,588,747| B2|   | 3/2020  | Allen       |           |
| 2016/0279019| A1| * | 9/2016 | Callow     | A61H 19/32|

(Continued)

FOREIGN PATENT DOCUMENTS

| EP | 2764847 A1    | 8/2013 |
| WO | 2016153844 A1 | 9/2016 |

OTHER PUBLICATIONS

Wassersug—"Non-pharmacological and non-surgical strategies to promote sexual recovery for men with erectile dysfunction". Translational Andrology and Urology, 2017, pp. S776-S794.

(Continued)

*Primary Examiner* — Samuel G Gilbert
(74) *Attorney, Agent, or Firm* — Mark P Kahler (57) ABSTRACT

To aid those with erectile disfunction, an anatomically erect penile prosthesis is disclosed that includes 1) an interior upper chamber that receives and houses the human penis, and 2) an interior lower chamber that receives and houses the human testicles. The prosthesis includes a flexible elongated member that provides a natural feeling substitute for the human penis that is contained within the interior upper chamber. The prosthesis includes an integral support mechanism that connects to the flexible elongated member to provide this natural feeling.

15 Claims, 9 Drawing Sheets

(56) References Cited

U.S. PATENT DOCUMENTS

2018/0098855 A1     4/2018   Crabb
2019/0388226 A1   12/2019   Crabb

OTHER PUBLICATIONS

Campbell—"A review of penile elongation surgery", Translational Andrology and Urology, 2017, pp. 69-78.
Chen—"Visualization of Penile Suspensory Ligamentous System Based on Visible Human Data Sets", Medical Science Monitor, 2017, vol. 23, pp. 2436-2444.
Hakky—"Penile Enhancement Procedures with Simultaneous Penile Prosthesis Placement", Hindawi Publishing Corporation, Advances in Urology, vol. 2012, Article ID 314612, 5 pages.
Lee—"Strategies for maintaining penile size following penile implant", AME Publishing Company, Translational Andrology and Urology, 2013, pp. 67-73.
Li—"The penile suspensory ligament: abnormalities and repair", BJU International, 2007, pp. 117-120.
Mec—"Suspensory ligament release for penile lengthening", downloaded from https://www.surgeonformen.com/suspensory-ligament-release-penile-lengthening/ on Mar. 26, 2020, Copyright 2001-2020, pp. 1-6.

\* cited by examiner

ANATOMICALLY ERECT PENILE PROSTHESIS WITH INTEGRAL SUSPENSORY MECHANISM

BACKGROUND

The disclosures herein relate generally to prosthetic apparatus for humans, and more particularly to penile prosthetic devices for human usage.

BRIEF SUMMARY

In one embodiment, a penile prosthesis includes a support base having front and back sides. An elongated member extends from the front side of the support base. The support base includes an upper cavity situated on the back side of the support base, wherein the upper cavity is configured to receive a human penis therein. The support base also includes a lower cavity situated on the back side of the support base, wherein the lower cavity is configured to receive human testicles therein. In one embodiment, the support base includes a J-shaped integral suspensory mechanism (ISM) having first and second ends, the first end of the J-shaped ISM being situated adjacent the upper cavity, the second end of the J-shaped ISM being connected to the elongated member.

In another embodiment, a penile prosthesis is disclosed that includes an elongated member that extends from a support base, wherein the support base includes a first cavity configured to receive a human penis therein and a second cavity configured to receive human testicles therein. The support base further includes a J-shaped integral suspensory mechanism (ISM) having first and second ends. The ISM includes an upper suspension support plate that provides the first end of the ISM. The ISM also includes a lower suspension anchor base that provides the second end of the ISM from which the elongated member extends. The ISM still further includes an intermediate suspension bridge connecting the upper suspension support plate and the lower suspension anchor base.

BRIEF DESCRIPTION OF THE DRAWINGS

The appended drawings illustrate only exemplary embodiments of the invention and therefore do not limit its scope because the inventive concepts lend themselves to other equally effective embodiments.

DETAILED DESCRIPTION

The disclosed prosthetic device aids penetrative sex for those with erectile dysfunction, commonly called "ED" in modern medical nomenclature. During normal sexual relations, the act of sexual intercourse involves the insertion of an erect male penis into the vagina of a female. In men with erectile dysfunction, there is difficulty with at least one stage of the sexual act.

One of the most common sexual problems that men experience is erectile dysfunction (ED). ED is characterized by the inability of the male to achieve or maintain an erection which may preclude the performance of the sexual act in a manner that is pleasing to both partners. Typical treatments for erectile dysfunction, in the order typically prescribed for ED patients, include pharmacologic agents, injections, vacuum devices, and surgical implants. Although these treatments have varying degrees of success, each has a drawback for one or both sexual partners. For example, the pharmacologic agents may have adverse side effects or drug-drug interactions that are harmful to the user. Mechanical devices such as vacuum pumps are cumbersome to use and require external bands to maintain results. Surgically implanted prostheses may not perform as expected and can be expensive to remove. The goal of pharmacological agents, mechanical devices, and surgical implants is to restore penis stiffness suitable for sexual intercourse. For many patients with ED, traditional treatments press human physiological capabilities to achieve an erect penis adequate for penetrative sex. Unwanted side effects, undesired results, and female partner dissatisfaction warrant efforts to invent non-medical and non-surgical protocols for managing erectile dysfunction.

Some attempted mechanical solutions seek to aid the individual with erectile dysfunction by externally applying a splint or other means to support the flaccid or semi-erect penis. Such devices generally fail in some manner to provide a suitably strong erection for repeated and natural physical intercourse. Further complicating the successful use of these mechanical devices is the unnatural feeling for the partner in the sexual act, thus further reducing or eliminating arousal for both partners. Sensitive tissues of the vaginal opening can sense the slightest difference caused by protruding edges, straps, or other mechanical devices supporting the penis. Simply put, mechanical devices thus far have failed to provide a true natural feeling to partners in physical intercourse. For example, such mechanical devices do not consider or account for the support that the male suspensory ligament provides the erect penis in anatomical physiology. The suspensory ligament supports the erect penis and restricts abduction movement of the penis to provide a pleasurable sensation against the inner vaginal wall.

The natural movements of the penis during penetrating vaginal intercourse are not uniaxial. In fact, the penis rotates minimally up and down through approximately 15° in the Sagittal plane with each thrusting cycle. These movements up and down vary from approximately 5° to approximately 20° with approximately 20° representing the angular restriction limit imposed on the penis by the suspensory ligament. When the male has a full erection, downward rotation is resisted by the natural upward curvature of the penis shaft in relation to the roots of the penis, as well as by the suspensory ligament of the penis. As in some mechanical devices, when the penis is hinged and thus not oriented upward, normal kinematics are impaired and can distract from the naturalness of the penetrative sex act. This, in turn, can lead to a less than fulfilling experience for one or both of the partners. The penile kinematics of the disclosed mechanical penile prosthesis device are intended to emulate anatomical function in multiple sex positions.

The disclosed mechanical penile prosthesis device provides an artificial erect penis when traditional medical treatment protocols are not desired. The disclosed prosthesis provides sexual satisfaction for both partners with a high rate of success, while avoiding the discomfort of traditional medical treatment protocols. The disclosed prosthesis provides for the primary physical sexual pleasure of the female partner. This apparatus further provides mutual physical and non-physical benefits with respect to sexual gratification for both partners.

Figure 1A:
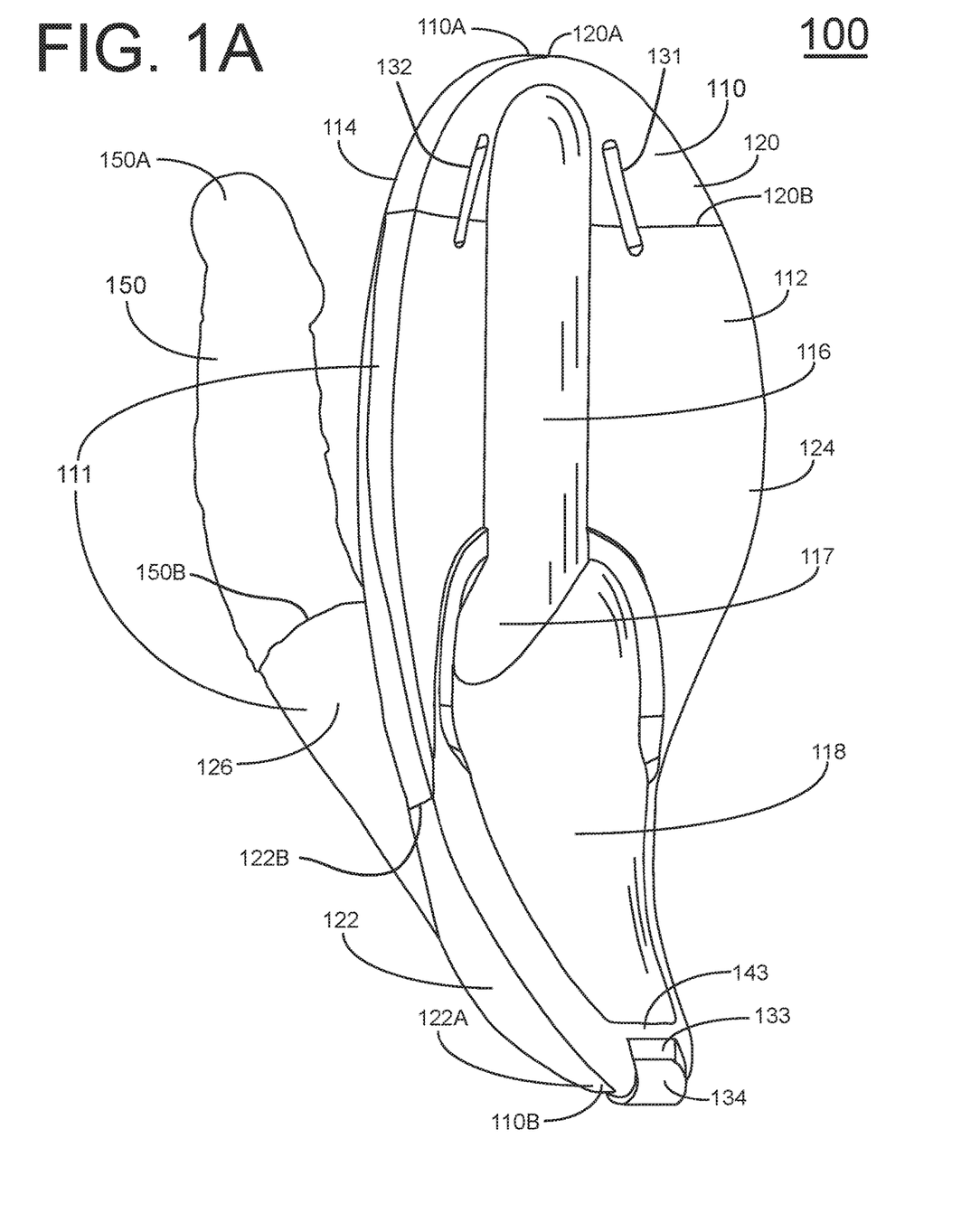
FIG. 1A is a rear perspective view of one embodiment of the disclosed penile prosthesis.
Figure 1B:
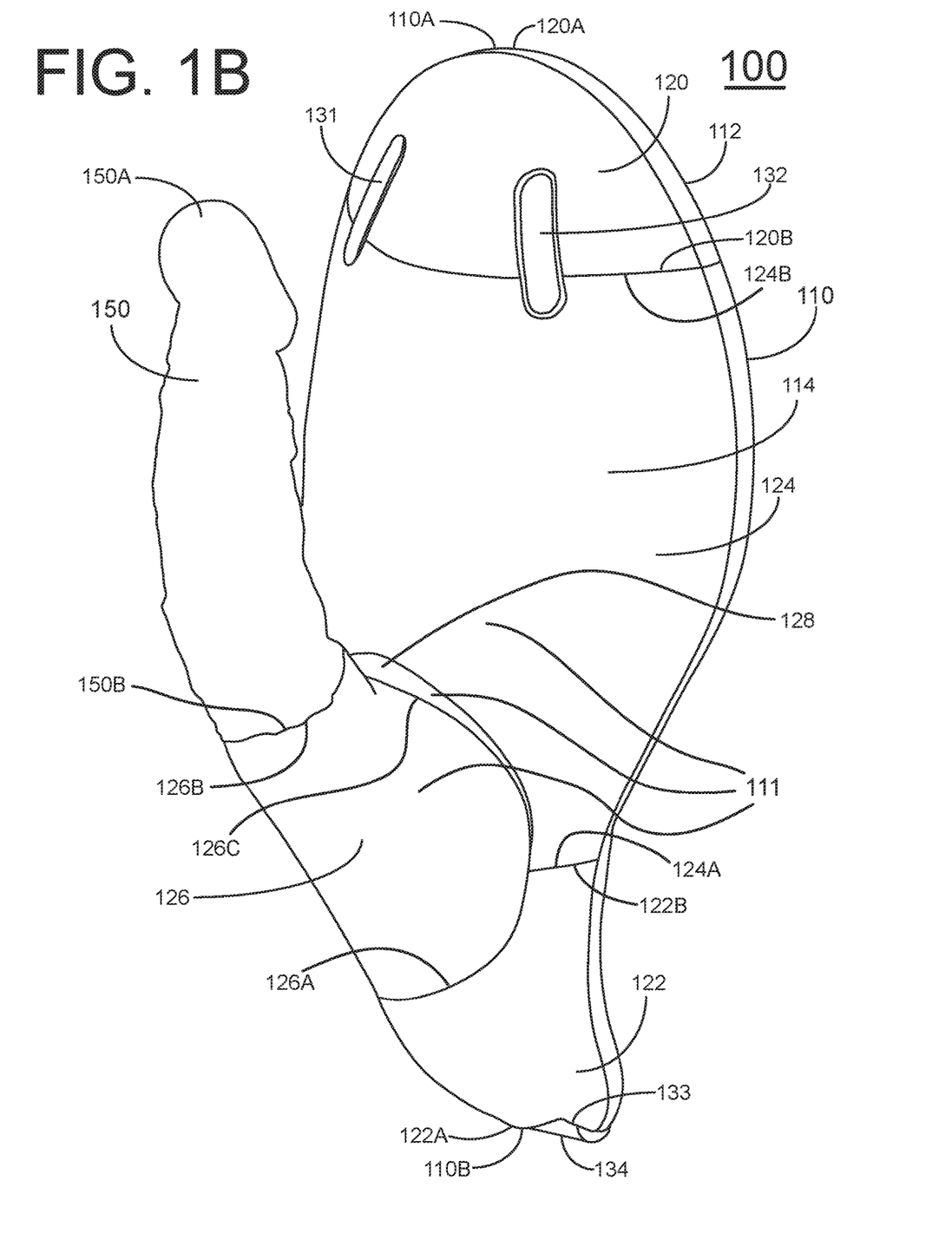
FIG. 1B is a front perspective view of one embodiment of the disclosed penile prosthesis.

The following is a list of elements that are referenced in FIGS. 1A-1I and this specification:
- 100 penile prosthesis
- 110 support base
- 110A support base top
- 110B support base bottom
- 111 integral suspensory mechanism
- 112 back side of prosthesis
- 114 front side of prosthesis
- 116 upper cavity
- 117 opening of upper cavity
- 118 lower cavity
- 119A, 119B opposed sides of lower cavity
- 120 upper mounting region
- 120A top end of upper mounting region
- 120B bottom end of upper mounting region
- 122 lower mounting region
- 122A bottom of lower mounting region
- 122B top end of lower mounting region
- 124 upper suspension support plate
- 124A bottom of upper suspension support plate
- 124B top of upper suspension support plate
- 126 lower suspension anchor base
- 126A bottom of lower suspension anchor base
- 126B top of lower suspension anchor base
- 126C side of lower suspension anchor base
- 128 intermediate suspension bridge
- 131 mounting slot
- 132 mounting slot
- 133 mounting slot
- 134 integral cylindrical member
- 140 left rim
- 140A upper left rim portion
- 140B lower left rim portion
- 142 right rim
- 142A upper right rim portion
- 142B lower right rim portion
- 143 bottom rim
- 145 perimeter of support base
- 150 elongated member
- 150A tip end of elongated member
- 150B base end of elongated member FIG. 1A is a rear perspective view of one embodiment of the disclosed penile prosthesis 100. Prosthesis 100 includes a support base 110 having a back side 112 and a front side 114, as seen in FIG. 1A and FIG. 1B, respectively. Referring again to FIG. 1A, the back side 112 of prosthesis 100 includes an upper cavity 116 and a lower cavity 118. Upper cavity 116 exhibits a penis-shaped geometry to receive the user's penis therein. Lower cavity 118 exhibits a geometry that is smoothly contoured to receive the user's testicles therein. In FIG. 1A, upper cavity 116 and lower cavity 118 each appear as depressions in back side 112 as indicated by appropriate shading.

Support base 110 includes an upper mounting region 120 that joins the top of upper suspension support plate 124, as shown in FIGS. 1A and 1B. Support base 110 also includes a lower mounting region 122 that joins the bottom of upper suspension support plate 124. Mounting regions 120 and 122 aid in mounting prosthesis 100 on the user, as discussed in more detail below.

Turning now to FIG. 1B, in one embodiment an elongated member 150 connects to and/or joins support base 110. In this particular embodiment, support base 110 includes an integral suspensory mechanism (ISM) 111 having 3 components, namely an upper suspension support plate 124, a lower suspension anchor base 126, and an intermediate suspension bridge 128 that connects lower suspension anchor base 126 to upper suspension support plate 124. ISM 111 is discussed in more detail below. In one embodiment, elongated member 150 exhibits an approximately cylindrical geometry. In another embodiment, elongated member 150 exhibits an approximately cylindrical geometry that is curved and/or arched upward as shown in FIG. 1B. Elongated member 150 may exhibit a penis-like shape that includes a tip end 150A and a base end 150B. Base end 150B of elongated member 150 integrates circumferentially into lower suspension anchor base 126. In one embodiment, elongated member 150 and lower suspension anchor base 126 may be fabricated of the same flexible material and formed together in the same mold during manufacture of prosthesis 100. In this manner, elongated member 150 integrally and/or seamlessly joins lower suspension anchor base 126 at base end 150B. In one embodiment, the geometry of base end 150B is circular, ovular, or similar to meet with a like circular, ovular, or similar geometry of top 126B of lower suspension anchor base 126. It is noted that in one embodiment, support base 110 includes all portions of prosthesis 100 except for the portion of prosthesis 100 that elongated member 150 provides. As explained in more detail below, in one embodiment all portions of prosthesis 100 including both support base 110 and elongated member 150 may be integrally formed in a common mold.

Returning to FIG. 1A, it is noted that upper cavity 116 opens into lower cavity 118 at an opening 117 that is formed therebetween. In this embodiment, upper mounting region 120 extends from the top end 120A of upper mounting region 120 to the bottom end 120B of upper mounting region 120. Upper mounting region 120 includes mounting slots 131 and 132 that receive respective upper straps of a conventional 3-point harness to assist in holding prosthesis 100 to the groin area of the user. Mounting slots 131 and 132 may extend partially into upper suspension support plate 124 as shown.

Mounting slots 131 and 132 are also visible in FIG. 1B as well as the figures that follow. It is noted that in this particular embodiment, lower cavity 118 becomes progressively narrower from opening 117 at the top of lower cavity 118 to mounting slot 133 that is adjacent the bottom of lower cavity 118 and adjacent the bottom 122A of lower mounting region 122. In this manner, lower cavity 118 is approximately V-shaped or U-shaped while exhibiting a generally contoured smooth interior to provide comfort to the user's testicles when placed in lower cavity 118. In this particular embodiment, lower mounting region 122 includes an integral substantially cylindrical member 134 adjacent mounting slot 133. Mounting slot 133 receives a lower strap of a conventional 3-point mounting harness to assist in holding prosthesis 100 to the groin area of the user. Cylindrical member 134 in combination with mounting slot 133 provides a convenient terminus around which a lower harness strap may be wrapped to secure prosthesis 100 to the user. In this embodiment, lower mounting region 122 extends from the bottom end 122A of lower mounting region 122 to the top end 122B of lower mounting region 122. More particularly and as seen in FIG. 1B, lower mounting region 122 extends from bottom end 122A to the adjacent lower surface 126A of lower suspension anchor base 126 and to the adjacent bottom 124A of upper suspension support plate 124. Lower suspension anchor base 126 includes bottom 126A, top 126B, and side 126C, as seen in FIG. 1B. In one embodiment, upper suspension support plate 124 and upper mounting region 120 exhibit a plate-like geometry.

Figure 1C:
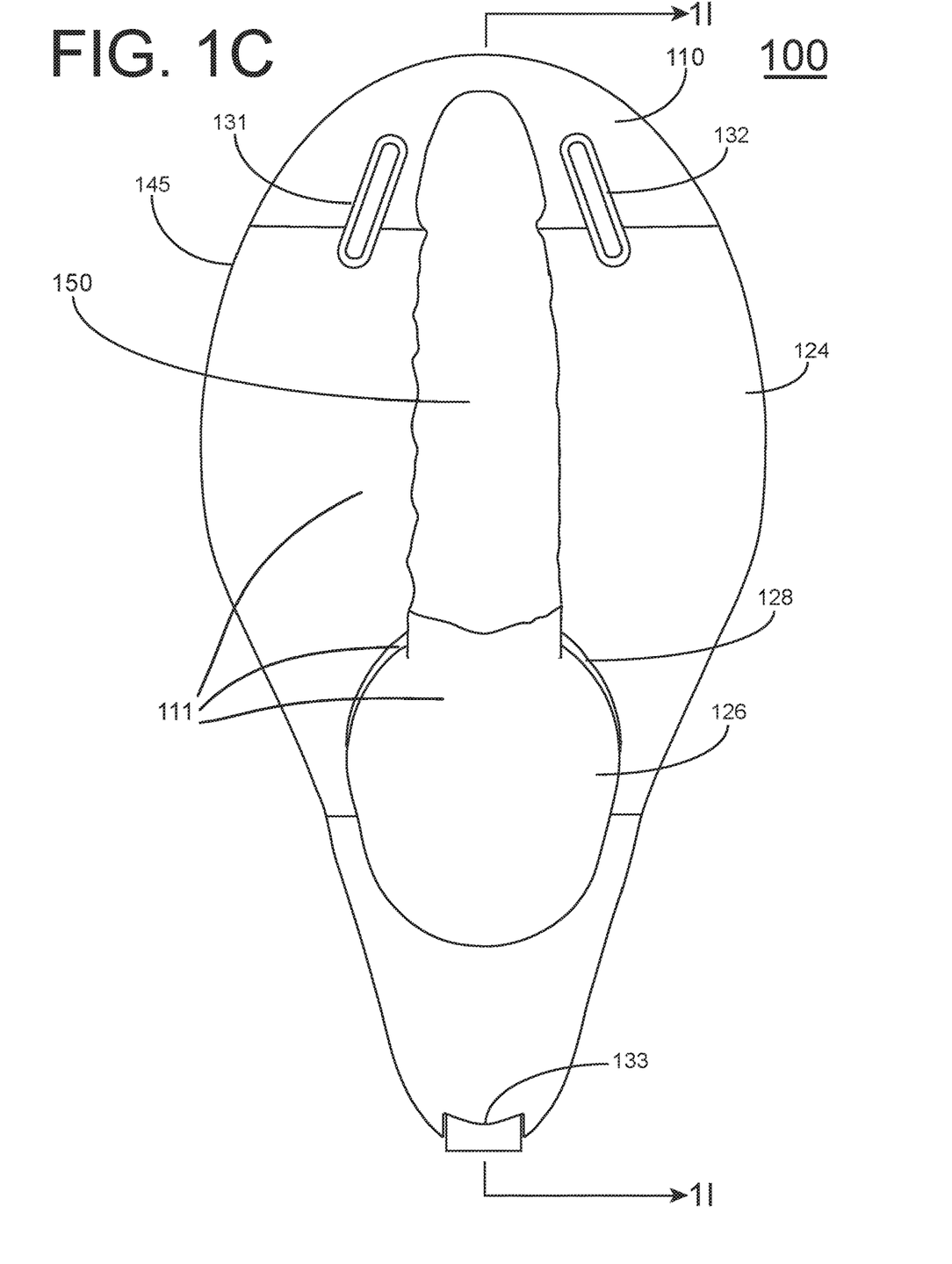
FIG. 1C is a front plan view of one embodiment of the disclosed penile prosthesis.

FIG. 1C is a front plan view of penile prosthesis 100 that depicts the integral suspensory mechanism (ISM) 111 as including: 1) upper suspension support plate 124, 2) lower suspension anchor base 126, and 3) intermediate suspension bridge 128. In one embodiment, these three elements taken together form a substantially J-shaped geometry ISM 111 that is readily observed in the cross section of penile prosthesis 100 shown in FIG. 1I and discussed below. ISM 111 forms part of the overall structure of support base 110 of prosthesis 100.

Figure 1D:
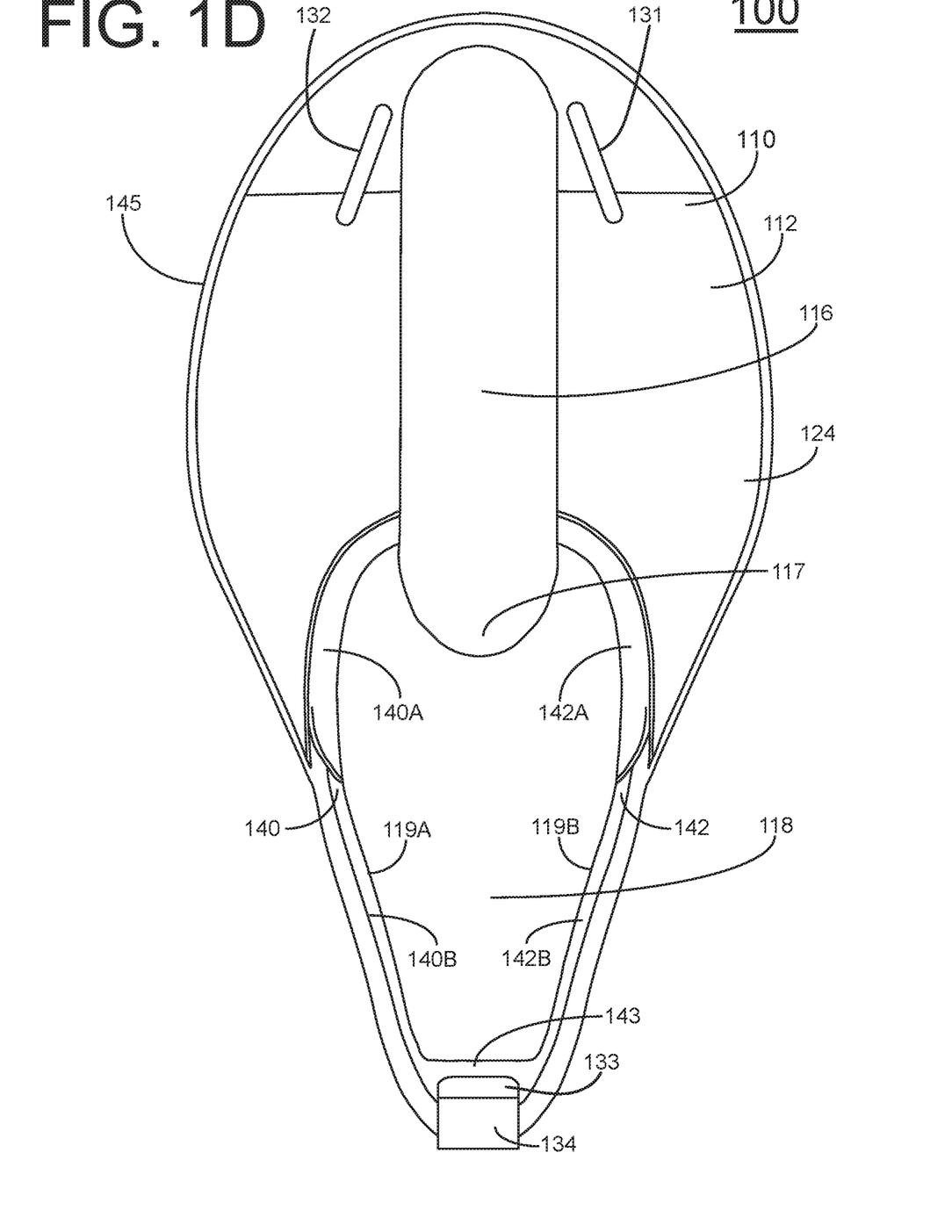
FIG. 1D is a rear plan view of one embodiment of the disclosed penile prosthesis.

FIG. 1D is a rear plan view of penile prosthesis 100 that depicts upper cavity 116 that is configured to receive a user's penis and lower cavity 118 that is configured to receiving the user's testicles. Referring now to lower cavity 118, a left rim 140 and a right rim 142 are situated on the opposed sides 119A and 119B, respectively, of lower cavity 118. Left rim 140 includes upper left rim portion 140A and lower left rim portion 140B. Right rim 142 includes upper right rim portion 142A and lower right rim portion 142B. A bottom rim 143 joins right rim 142 and left rim 140 together as shown. In one embodiment, the geometry of rims 140, 142 and 143 forms an inverted U that comfortably contacts the groin region of the user's body when the user wears penile prosthesis 100. In one embodiment, the entire perimeter 145 of prosthesis back side 112 can be rounded for the user's comfort when prosthesis 100 is mounted to the user.

Figure 1E:
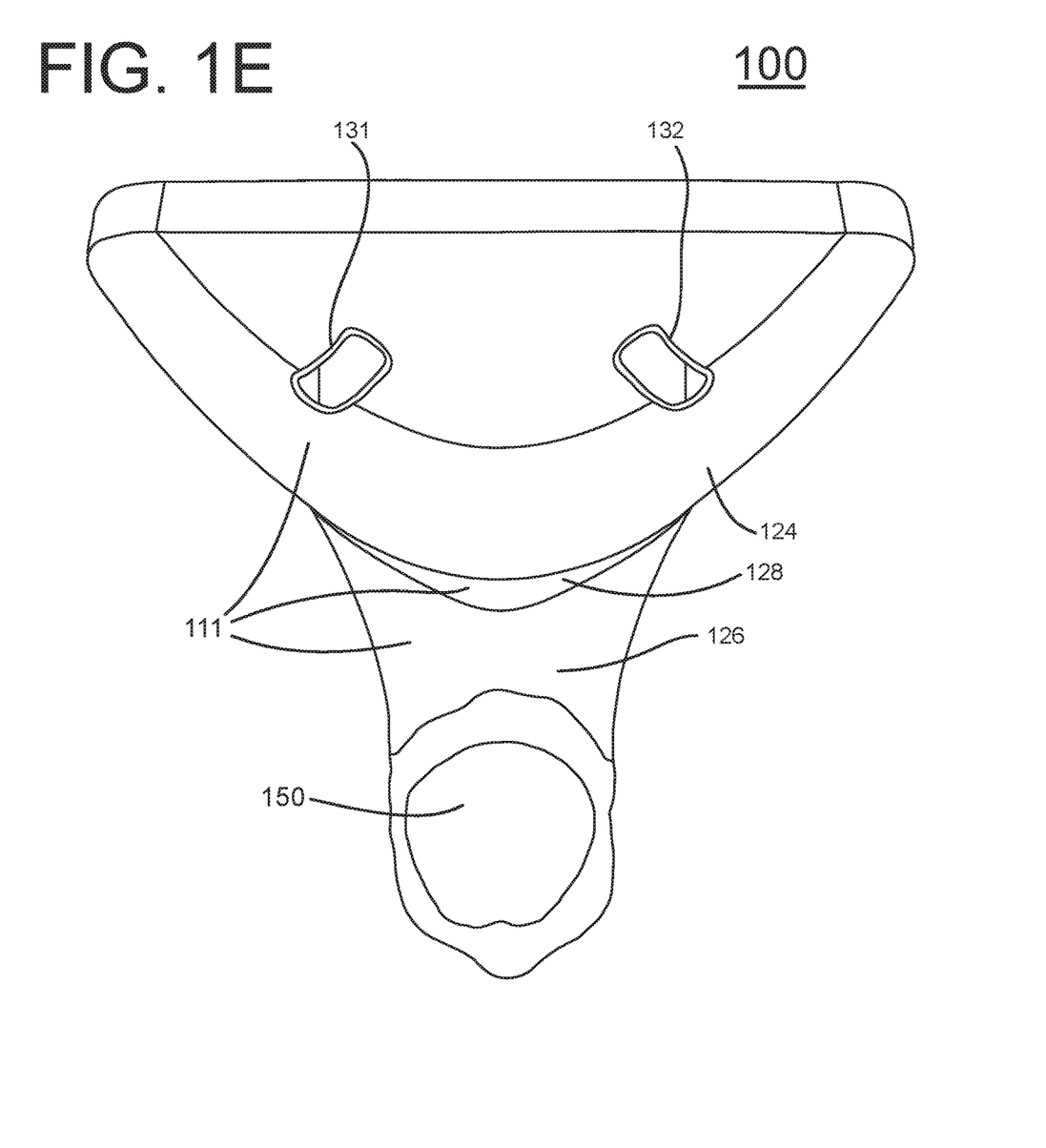
FIG. 1E is a top plan view of one embodiment of the disclosed penile prosthesis.
Figure 1F:
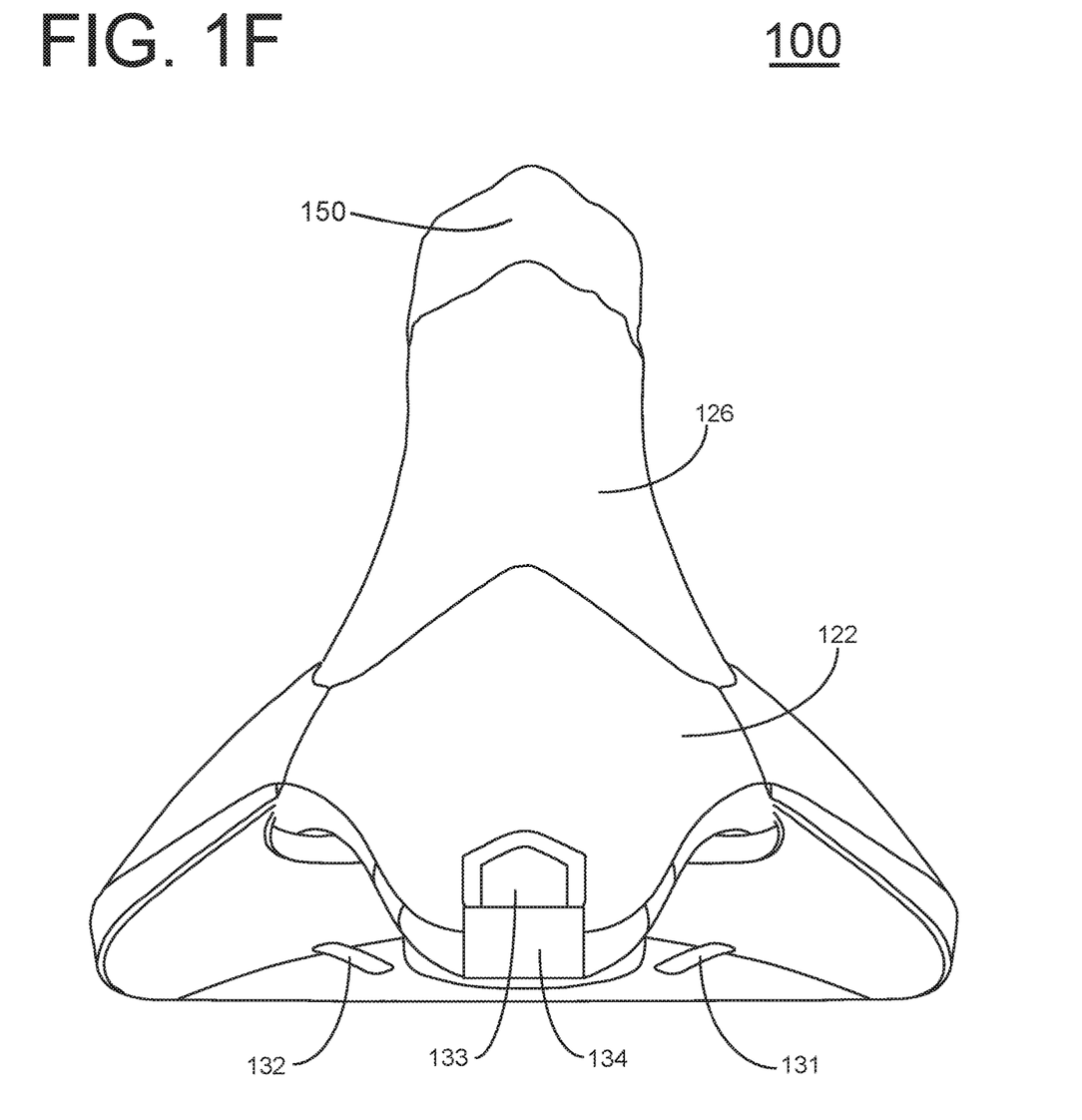
FIG. 1F is a bottom plan view of one embodiment of the disclosed penile prosthesis.

FIG. 1E is a top plan view of penile prosthesis 100 that shows integral suspensory mechanism (ISM) 111 as including upper suspension support plate 124, lower suspension anchor base 126, and intermediate suspension bridge 128. FIG. 1F shows a bottom plan view of penile prosthesis 100. It is again noted that mounting slot 133 together with integral cylinder 134 provides a convenient terminus to engage one of the straps of a multi-point harness when penile prosthesis 100 is mounted on the human user.

Figure 1G:
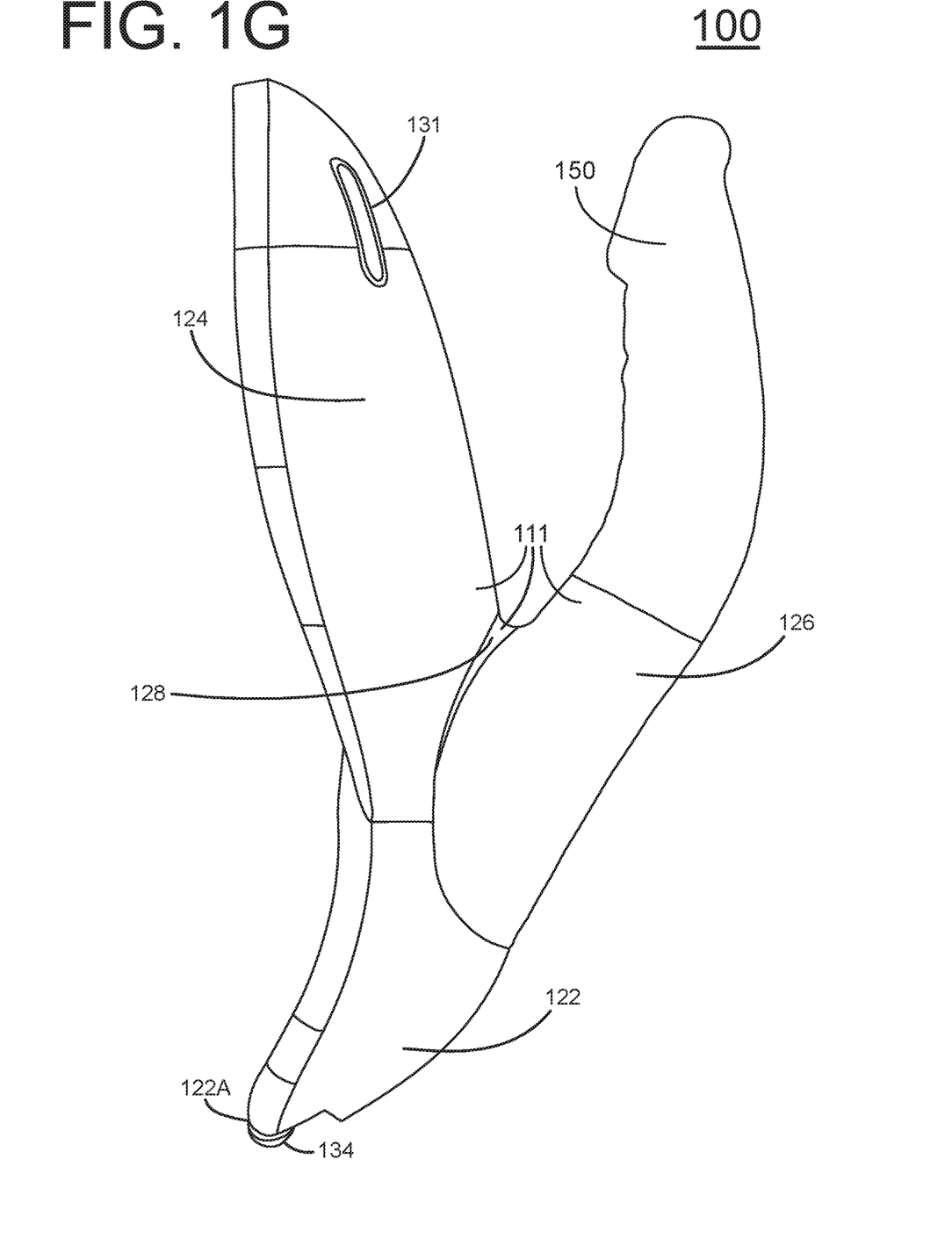
FIG. 1G is left plan view of one embodiment of the disclosed penile prosthesis.
Figure 1H:
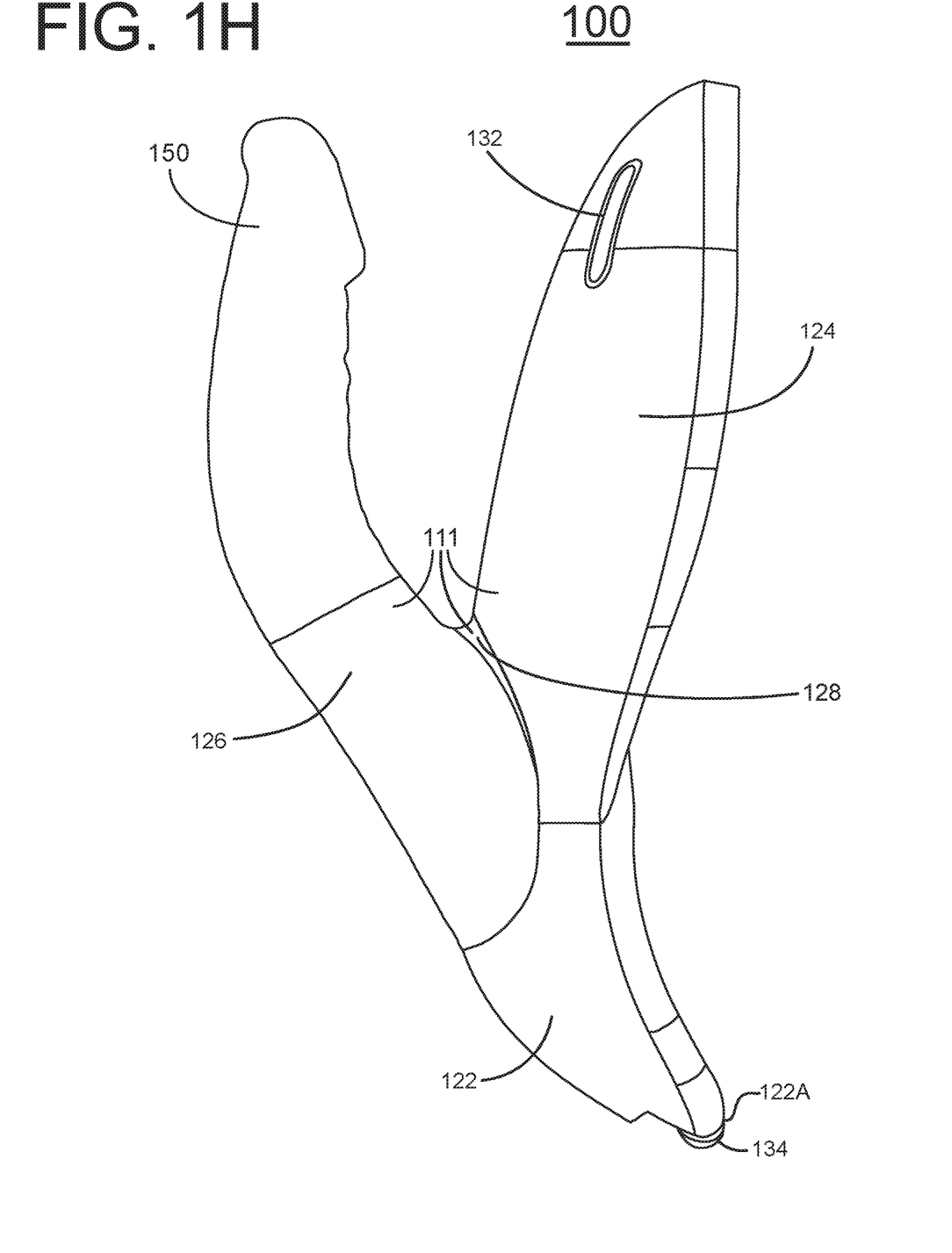
FIG. 1H is a right plan view of one embodiment of the disclosed penile prosthesis.

FIG. 1G is a left plan view of penile prosthesis 100 that shows integral suspensory mechanism (ISM) 111 as being substantially J-shaped. It is noted for reference that the letter J includes a long arm and a short arm, the bottoms of which are joined together with a U-shaped geometry. Applying this description now to ISM 111 of prosthesis 100 of FIG. 1G, upper suspension support plate 124 provides the long arm of the J, while lower suspension anchor base 126 provides the short arm of the J. Intermediate suspension bridge 128 and the lowermost portions of plate 124 and base 126 provide the U-shaped bottom portion of ISM 111. FIG. 1H is a right plan view of penile prosthesis 100 that is the mirror image of the left plan view of FIG. 1G. The discussion above with respect to the left plan view of prosthesis 100 of FIG. 1G applies as well to the right plan view of prosthesis 100 of FIG. 1H, and is thus not repeated here.

Figure 1I:
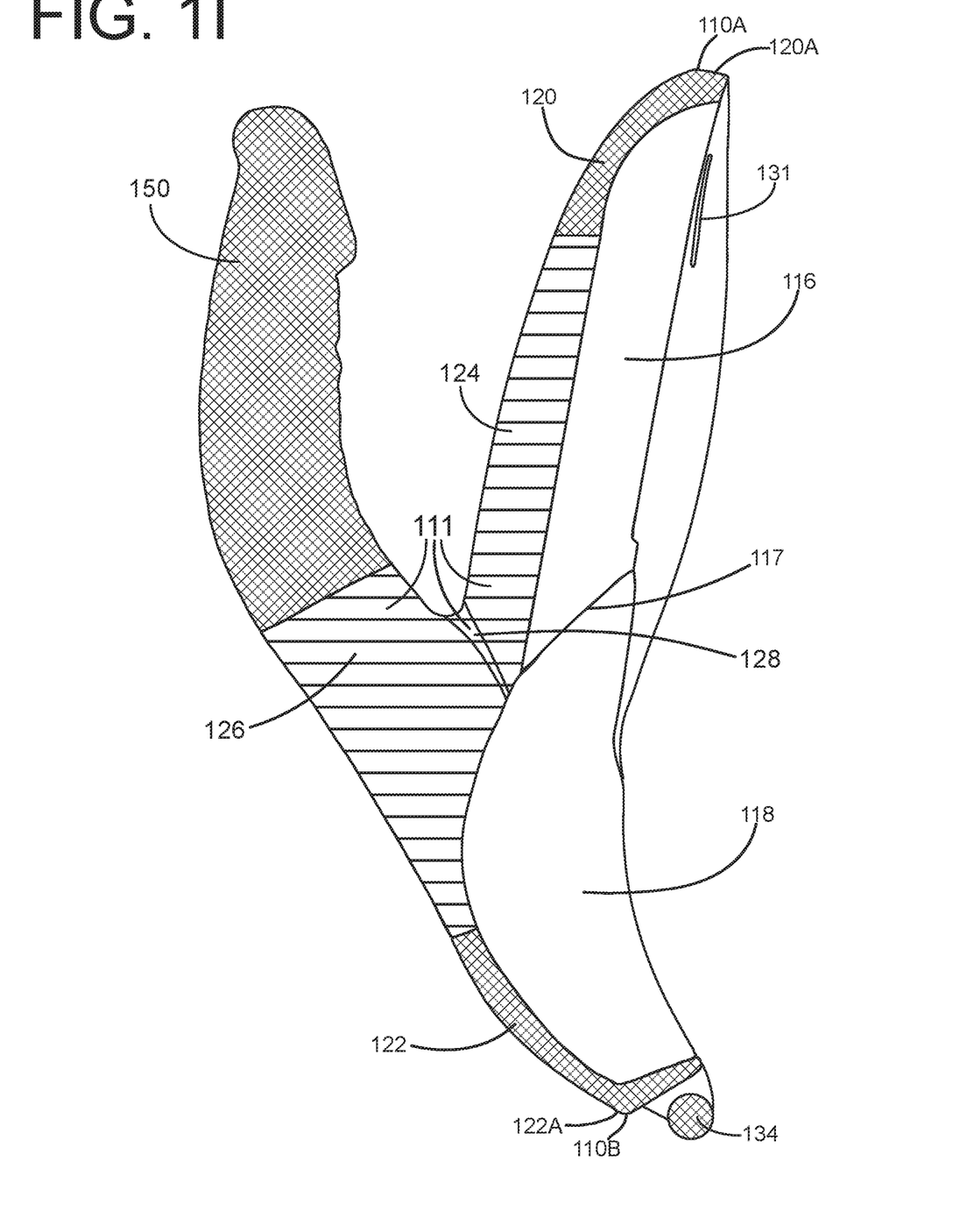
FIG. 1I is a cross sectional view of one embodiment of the disclosed penile prosthesis.

FIG. 1I is a cross sectional view of penile prosthesis 100 taken along section line 1I-1I of FIG. 1C. This cross sectional view uses the same hatching pattern for the 3 regions of integral suspensory mechanism (ISM) 111, namely for upper suspension support plate 124, lower suspension anchor base 126 and intermediate suspension bridge 128. Usage of the same hatching pattern for these 3 components of ISM 111 indicates that all of these components can be integrally formed of the same material, for example an elastomer such as silicone. While the remaining portions of prosthesis 100, such as elongated member 150, upper mounting region 120 and lower mounting region 122 are shown with a different hatching pattern than ISM 111 for purposes of illustration, in one embodiment all components of prosthesis 100 may be formed from the same elastomeric material in a single mold during manufacture. In this manner, each component of prosthesis 100 integrally blends into the next adjacent component to form a single unitary structure.

FIG. 1I shows an embodiment of prosthesis 100 wherein integral suspensory mechanism (ISM) 111 exhibits a substantially J-like shape or geometry. This geometric configuration has been found to provide the human female with pleasurable sensations similar to those provided by the suspensory ligament that anatomically supports the male erect human penis during penetrative sex. ISM 111 restricts the rotation of the erect penis in the Saggital plane, thus creating an opposing equal pressure on the interior vaginal wall during intercourse providing friction for arousal.

Advantageously, embodiments of the disclosed prosthesis are useful in cases where a human user does not have functioning male genitalia. For example, the disclosed external prosthesis enables a male with erectile disfunction (ED) to effectively penetrate a partner without resorting to surgery, injections, vacuum devices or medications. The user wears the prosthesis for intercourse and removes the prosthesis when done. In one embodiment, the disclosed prosthesis is made of an elastomer such as pure medical grade silicone. When fabricated from pure silicone, the disclosed prosthesis includes no phthalates and no polyvinyl chloride (PVC). Other rubber-like flexible materials, polymers and synthetics may also be used to fabricate the disclosed prosthesis. The prosthesis is non-porous and easy to clean.

Prosthesis 100 conforms to the human body groin area to provide a comfortable fit for the user. The configuration of integral support mechanism (ISM) 111 gives the female a sensation similar to that provided by the suspensory ligament that supports the erect human penis during penetration. The prosthesis performs well in cases of total erectile failure. Prosthesis 100 is useable in multiple scenarios when user exhibits conditions such as a flaccid, semi-erect, or erect penis with accommodations within the interior cavities of prosthesis 100. Not only is the human penis accommodated internal to prosthesis 100, but prothesis 100 also includes an external elongated member 150 that readily substitutes for the user's own penis. Prosthesis 100 is flexible and moves with the body to provide natural degrees of movement. Prothesis 100 also performs successfully in cases where the user has no penis and/or testicles due to injury or other reasons. The prosthesis is both easy to attach and remove to the human body.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be also understand that the terms "including" and "having" are synonymous.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Process steps may be performed in an order different than those presented for purposes of example. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A penile prosthesis, comprising:
   a support base including front and back sides;
   a flexible solid elongated member extending from the front side of the support base;
   the support base including:
      an upper cavity situated to extend along the back side of the support base, wherein the upper cavity is configured to receive a human penis therein;
      a lower cavity situated on the back side of the support base, wherein the lower cavity is configured to receive and contain human testicles internal to the lower cavity; and
      a J-shaped integral suspensory mechanism (ISM) having first and second ends, the first end of the J-shaped ISM being situated adjacent the upper cavity, the second end of the J-shaped ISM being connected to the elongated member.

2. The penile prosthesis of claim 1, wherein the J-shaped integral suspensory mechanism (ISM) comprises:
   an upper suspension support plate that includes at least a portion of the upper cavity of the support base;
   a lower suspension anchor base that is adjacent at least a portion of the lower cavity of the support base, the lower suspension anchor base connecting to the elongated member; and
   an intermediate suspension bridge connecting the upper suspension support plate to the lower suspension anchor base.

3. The penile prosthesis of claim 2, wherein the elongated member includes a tip end and a base end, the base end being connected to the lower suspension anchor base, the elongated member being curved from the tip end to the base end.

4. The penile prosthesis of claim 1, wherein the support base further comprises:
   at least one upper mounting structure adjacent the upper cavity of the support base; and
   at least one lower mounting structure adjacent the lower cavity of the support base.

5. The penile prosthesis of claim 4, wherein the at least one upper mounting structure and the at least one lower mounting structure comprise slots that are attachable to a harness to hold the penile prosthesis in position on a human user.

6. The penile prosthesis of claim 1, wherein the support base and the elongated member comprise a flexible elastomer.

7. The penile prosthesis of claim 1, wherein the elongated member exhibits a penis-like shape.

8. The penile prosthesis of claim 1, wherein the upper cavity opens into the lower cavity.

9. A penile prosthesis, comprising:
   a flexible solid elongated member that extends from a support base;
   the support base including:
      a first cavity configured to receive a human penis therein;
      a second cavity configured to receive human testicles therein, and
      a J-shaped integral suspensory mechanism (ISM) having first and second ends, wherein the ISM includes:
         an upper suspension support plate providing the first end of the ISM;
         a lower suspension anchor base providing the second end of the ISM from which the elongated member extends, and
         an intermediate suspension bridge connecting the upper suspension support plate and the lower suspension anchor base.

10. The penile prosthesis of claim 9, wherein the support base comprises:
    at least one upper mounting structure adjacent the upper cavity of the support base;
    at least one lower mounting structure adjacent the lower cavity of the support base.

11. The penile prosthesis of claim 10, wherein the at least one upper mounting structure and the at least one lower mounting structure comprise slots that are attachable to a harness to hold the penile prosthesis in position on a human user.

12. The penile prosthesis of claim 9, wherein the elongated member exhibits a penis-like shape.

13. The penile prosthesis of claim 9, wherein the first cavity opens into the second cavity.

14. The penile prosthesis of claim 9, wherein the elongated member includes a tip end and a base end, the base end being connected to the lower suspension anchor base, the elongated member being curved from the tip end to the base end.

15. The penile prosthesis of claim 9, wherein the support base and the elongated member comprise a flexible elastomer.

* * * * *